(12) United States Patent
Duval et al.

(10) Patent No.: US 11,413,164 B2
(45) Date of Patent: Aug. 16, 2022

(54) LEG LENGTH CALCULATION IN COMPUTER-ASSISTED SURGERY

(71) Applicant: ORTHOSOFT INC., Montreal (CA)

(72) Inventors: Karine Duval, Montreal (CA); Di Li, LaSalle (CA); Laurence Moreau-Belanger, Laval (CA); Benoit Pelletier, Laval (CA); Yvan Leone, Montreal (CA); Myriam Valin, Laval (CA); François Paradis, Boucherville (CA)

(73) Assignee: ORTHOSOFT ULC, Montreal (CA)

( * ) Notice: Subject to any disclaimer, the term of this patent is extended or adjusted under 35 U.S.C. 154(b) by 423 days.

(21) Appl. No.: 16/535,659

(22) Filed: Aug. 8, 2019

(65) Prior Publication Data
US 2019/0358059 A1    Nov. 28, 2019

Related U.S. Application Data

(62) Division of application No. 15/013,285, filed on Feb. 2, 2016, now Pat. No. 10,413,428.
(Continued)

(51) Int. Cl.
*A61B 5/107* (2006.01)
*A61F 2/46* (2006.01)
(Continued)

(52) U.S. Cl.
CPC .......... *A61F 2/4657* (2013.01); *A61B 5/1072* (2013.01); *A61B 5/1075* (2013.01);
(Continued)

(58) Field of Classification Search
CPC ............ A61F 2/4657; A61F 2002/4658; A61F 2002/469; A61B 5/1072; A61B 5/1075;
(Continued)

(56) References Cited

U.S. PATENT DOCUMENTS

| 5,122,145 A | 6/1992 | Fishbane |
| 5,682,886 A | 11/1997 | Delp et al. |

(Continued)

FOREIGN PATENT DOCUMENTS

| CN | 102413773 A | 4/2012 |
| WO | 2014197451 A1 | 12/2014 |

OTHER PUBLICATIONS

Barbier, et al. "Interest of an intraoperative limb-length and offset measurement device in total hip arthroplasty." Orthopaedics & Traumatology: Surgery & Research 98.4 (2012): 398-404.
(Continued)

*Primary Examiner* — David J. McCrosky
(74) *Attorney, Agent, or Firm* — Norton Rose Fulbright Canada LLP

(57) ABSTRACT

A computer-assisted surgery system has inertial sensor unit connected to an instrument and producing readings representative of its orientation. A computer-assisted surgery processor unit has a coordinate system module for setting a pelvic coordinate system from readings of the inertial sensor unit when the instrument is in a given orientation relative to the pelvis, a tracking module for tracking an orientation of the instrument relative to the pelvic coordinate system during movements thereof and a geometrical relation data module for recording preoperatively a landmark orientation relative to the pelvic coordinate system and a distance when the at least one instrument has a first end abutted to a pelvic landmark and a second end abutted to a leg landmark, for recording after implant rejointing the medio-lateral orientation and the distance, and for calculating a leg length discrepancy and/or an offset, based on the distances and the medio-lateral orientations.

8 Claims, 13 Drawing Sheets

Related U.S. Application Data

(60) Provisional application No. 62/110,861, filed on Feb. 2, 2015.

(51) Int. Cl.
*A61B 34/20* (2016.01)
*A61B 5/00* (2006.01)
*A61B 34/00* (2016.01)
*A61B 17/84* (2006.01)
*G01B 21/04* (2006.01)
*A61B 90/00* (2016.01)

(52) U.S. Cl.
CPC .......... *A61B 5/1079* (2013.01); *A61B 5/6829* (2013.01); *A61B 5/6838* (2013.01); *A61B 17/848* (2013.01); *A61B 34/20* (2016.02); *A61B 34/25* (2016.02); *A61B 2034/2048* (2016.02); *A61B 2090/061* (2016.02); *A61F 2002/469* (2013.01); *A61F 2002/4658* (2013.01); *G01B 21/04* (2013.01); *G01B 2210/40* (2013.01); *G01B 2210/58* (2013.01)

(58) Field of Classification Search
CPC ... A61B 5/1079; A61B 5/6829; A61B 5/6838; A61B 17/848; A61B 34/20; A61B 34/25; A61B 2034/2048; A61B 2090/061; G01B 21/04; G01B 2210/58
See application file for complete search history.

(56) References Cited

U.S. PATENT DOCUMENTS

| | | |
|---|---|---|
| 6,978,167 B2 | 12/2005 | Dekel |
| 7,001,346 B2 | 2/2006 | White |
| 8,133,229 B1 | 3/2012 | Bonutti |
| 8,588,892 B2 | 11/2013 | Hladio |
| 2006/0293614 A1 | 12/2006 | Radinsky |
| 2007/0021644 A1 | 1/2007 | Woolson |
| 2009/0125117 A1 | 5/2009 | Paradis et al. |
| 2009/0248044 A1 | 10/2009 | Amiot et al. |
| 2010/0137869 A1 | 6/2010 | Borja et al. |
| 2011/0009285 A1 | 4/2011 | Mayer |
| 2011/0092858 A1 | 4/2011 | Burger |
| 2012/0022406 A1 | 1/2012 | Hladio |
| 2012/0316563 A1 | 12/2012 | Metzger et al. |
| 2013/0274633 A1 | 10/2013 | Hladio |
| 2014/0031829 A1 | 1/2014 | Paradis et al. |
| 2014/0330281 A1 | 11/2014 | Aghazadeh |
| 2015/0142372 A1 | 5/2015 | Singh |
| 2016/0367382 A1 | 12/2016 | Zaima et al. |

OTHER PUBLICATIONS

Hill, J. C., et al. "Using a calliper to restore the centre of the femoral head du ring total hip replacement." J Bone Joint Surg Br 94.11 (2012): 1468-1474.

Desai, et al. "Leg length discrepancy after total hip arthroplasty: a review of literature." Current reviews in musculoskeletal medicine 6.4 (2013): 336-341.

Rice, et al. "Three intraoperative methods to determine limb-length discrepancy in THA" Orthopedies 37.5 (2014): e488-e495.

LEG LENGTH CALCULATION IN COMPUTER-ASSISTED SURGERY

CROSS-REFERENCE TO RELATED APPLICATION

The present application is a divisional of U.S. patent application Ser. No. 15/013,285, filed on Feb. 2, 2016 which claims priority of U.S. Provisional Patent Application No. 62/110,861, filed on Feb. 2, 2015, and incorporated herein by reference.

TECHNICAL FIELD

The present disclosure relates to a system and method used in Computer-Assisted Surgery (CAS) to provide leg length discrepancy and offset measurements, for instance in hip surgery.

BACKGROUND OF THE ART

In orthopedic surgery, for instance hip replacement, leg length discrepancy is a change of leg length along the longitudinal axis of the patient, between a pre-operative length and an intra-operative or post-operative length. Also in hip replacement, offset is the measurement of the translational shift of the leg along a medio-lateral axis of the patient, at the hip joint. Both these parameters are relevant during hip surgery, including total hip replacement, acetabular cup implanting, femoral implanting (e.g., head and neck implant, resurfacing). Hence, there is a need for systems and methods for determining leg length discrepancy and offset that is minimally invasive yet precise and accurate.

SUMMARY

It is aim of the present disclosure to provide novel systems and methods for determining leg length discrepancy and offset to assess orthopedic hip surgery.

Therefore, in accordance with a first embodiment of the present disclosure, there is provided a computer-assisted surgery system for outputting at least one of a leg length discrepancy and an offset between a preoperative leg condition and a post-implant rejointing leg condition comprising: at least one instrument; at least one inertial sensor unit connected to the at least one instrument, the inertial sensor unit producing readings representative of its orientation; a computer-assisted surgery processor unit operating a surgical assistance procedure and comprising a coordinate system module for setting a pelvic coordinate system from readings of the at least one inertial sensor unit when the at least one instrument is in a given orientation relative to the pelvis, a tracking module for tracking an orientation of the at least one instrument relative to the pelvic coordinate system during movements thereof using the readings from the inertial sensor unit on the instrument, and a geometrical relation data module for recording preoperatively a medio-lateral orientation of the at least one instrument representative of a medio-lateral axis of the legs relative to the pelvic coordinate system and a distance between the legs along the medio-lateral axis, for recording after implant rejointing the medio-lateral orientation and said distance, and for calculating at least one of a leg length discrepancy and an offset, based on said distances and said medio-lateral orientations; an interface for outputting at least the leg length discrepancy or the offset between the preoperative leg condition and the post-implant rejointing leg condition.

Further in accordance with the first embodiment, the at least one instrument is a caliper having a body with a translational joint for expanding/contracting, and legs configured for abutment with pelvic landmarks.

Still further in accordance with the first embodiment, the at least one instrument supports a light source emitting a light beam that is perpendicular relative to a direction of the translational joint.

Still further in accordance with the first embodiment, the light source is displaceable along the body, the light beam being a leg alignment marker when the caliper is abutted against the pelvic landmarks.

Still further in accordance with the first embodiment, the given orientation has a direction of the translational joint parallel to a medio-lateral axis of the pelvis.

Still further in accordance with the first embodiment, an ankle clamp has ankle interfaces configured to remain fixed to the ankles, with linkages interconnecting the ankle interfaces.

Still further in accordance with the first embodiment, a scale in the linkages measures the distance.

Still further in accordance with the first embodiment, the linkages include at least a translational joint in a direction generally aligned with a medio-lateral axis between the legs.

Still further in accordance with the first embodiment, indicators are provided for receiving ends of the caliper for recording the medio-lateral orientation with the caliper abutted against the ankle clamp.

Still further in accordance with the first embodiment, the at least one instrument is an acetabular-implant impactor, and wherein the impactor supports a light source emitting a light beam having a known orientation relative to a longitudinal axis of the impactor.

Still further in accordance with the first embodiment, the given orientation has the light beam illuminating the medio-lateral axis of the pelvis, with a shaft of the impactor lying in a plane of the light beam.

Still further in accordance with the first embodiment, an ankle clamp has ankle interfaces configured to remain fixed to the ankles, with linkages interconnecting the ankle interfaces, the ankle clamp further comprising indicators for being illuminated by the light beam for recording the medio-lateral orientation.

Still further in accordance with the first embodiment, a scale is in the linkages to measure the distance.

In accordance with a second embodiment of the present disclosure, there is provided a computer-assisted surgery system for outputting at least one of a leg length discrepancy and an offset between a preoperative leg condition and a post-implant rejointing leg condition comprising: at least one instrument; at least one inertial sensor unit connected to the at least one instrument, the inertial sensor unit producing readings representative of its orientation; a computer-assisted surgery processor unit operating a surgical assistance procedure and comprising a coordinate system module for setting a pelvic coordinate system from readings of the at least one inertial sensor unit when the at least one instrument is in a given orientation relative to the pelvis, a tracking module for tracking an orientation of the at least one instrument relative to the pelvic coordinate system during movements thereof using the readings from the inertial sensor unit on the instrument, and a geometrical relation data module for recording preoperatively a landmark orientation relative to the pelvic coordinate system and a distance when the at least one instrument has a first end abutted to a pelvic landmark and a second end abutted to a leg landmark, for recording after implant rejointing the landmark orientation and said distance, and for calculating at least one of a leg length discrepancy and an offset, based on said distances and said landmark orientations; an interface for outputting at least the leg length discrepancy or the offset between the preoperative leg condition and the post-implant rejointing leg condition.

Further in accordance with the second embodiment, the at least one instrument is a caliper having a body with a translational joint for expanding/contracting, and legs configured for contacting the pelvic landmark and the leg landmark.

Still further in accordance with the second embodiment, the caliper supports a light source emitting a light beam that is perpendicular relative to a direction of the translational joint.

Still further in accordance with the second embodiment, the given orientation has the light beam illuminating the medio-lateral axis of the pelvis.

Still further in accordance with the second embodiment, a scale is on the translational joint to obtain said distances.

Still further in accordance with the second embodiment, the at least one instrument includes a mechanical gauge having body with a translational joint for expanding/contracting, and bores configured for being connected to pins constituting the pelvic landmark and the leg landmark.

Still further in accordance with the second embodiment, a scale is on the translational joint to obtain said distances.

Still further in accordance with the second embodiment, the at least one instrument includes an acetabular-implant impactor supporting the inertial sensor unit, and wherein the impactor supports a light source emitting a light beam having a known orientation relative to a longitudinal axis of the impactor.

Still further in accordance with the second embodiment, the given orientation has the light beam illuminating the medio-lateral axis of the pelvis, with a shaft of the impactor lying in a plane of the light beam.

Still further in accordance with the second embodiment, the landmark orientation has the light beam illuminating a longitudinal axis of the mechanical gauge, with a shaft of the impactor lying in a plane of the light beam.

In accordance with the third embodiment of the present disclosure, there is provided a method for repeating a leg alignment between a preoperative leg condition and a post-implant rejointing leg condition, comprising: pre-operatively, with the patient in supine decubitus, orienting a light source using landmarks on the pelvis to produce a light beam aligned with a transverse plane of the pelvis, positioning at least one of the legs of the patient in alignment with the light beam, and setting landmarks on the legs of the patient, distally from the pelvis; post post-implant rejointing, with the patient in supine decubitus, repeating the orienting and the positioning, and noting a movement of the ladmarks.

Still further in accordance with the third embodiment, setting landmarks on the legs of the patient comprises projecting a light beam from a landmark on a first of the legs onto a scale on a landmark on a second of the legs.

Still further in accordance with the first embodiment, noting a movement of the landmarks comprises at least noting a displacement of the light beam on the scale.

Still further in accordance with the first embodiment, wherein noting a movement of the landmarks comprises at least noting a variation of distance between the landmarks.

DETAILED DESCRIPTION

Figure 1:
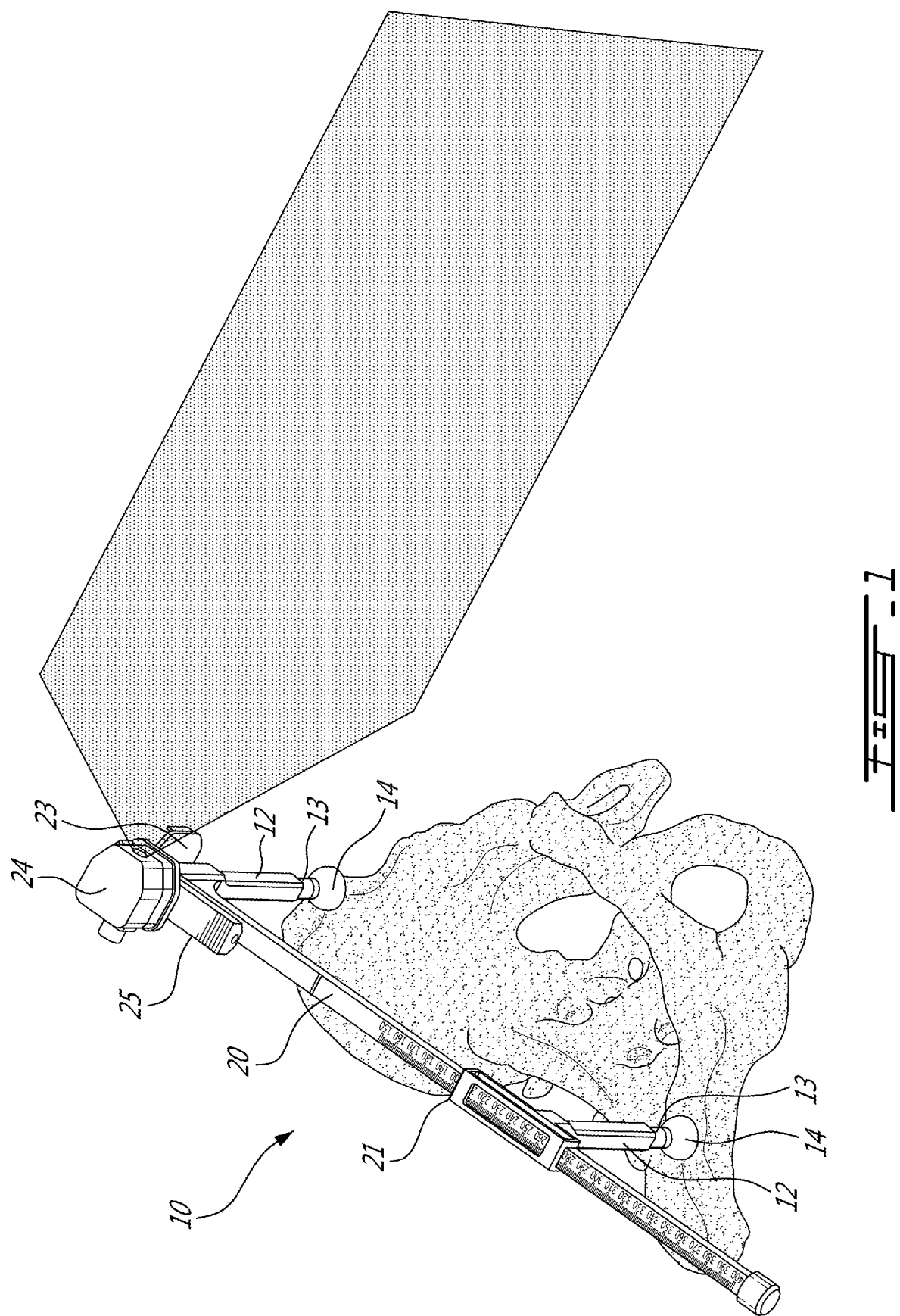
FIG. 1 is a perspective view of a caliper instrument on a pelvis during a leg positioning technique.

In the proposed disclosure, the leg length discrepancy and offset measurements are resolved using basic trigonometry. Leg length discrepancy and/or offset are measured to quantify the post-operative gait of the patient, to diagnose a patient condition, to assist in a physiotherapy treatment, or even to perform corrective actions intra-operatively, among numerous other possibilities. The measurements may be performed on a patient during hip replacement surgery, or can be performed on a bone model or cadaver. In general, the distance measurements are obtained based on the readings from mechanical instruments. The use of inertial sensors may assist in giving precision and accuracy to the aforementioned measurements. For example, as shown in FIG. 1, a caliper instrument 10 may be used. The caliper instrument 10 is described in US Patent Application Publication No. 2014/0031829, incorporated herein by reference, and uses inertial sensor technology.

As shown in FIG. 1, the caliper instrument 10 may be used as part of a bone digitizer in a bone digitizing system, to create a frame of reference for subsequent navigation of tools relative to bones in surgery, for instance based on the determination of the medio-lateral axis of the pelvis. The instrument 10 is referred to as a caliper, as it features a pair of legs 12 movable relative to one another, e.g., in a telescopic manner. The expression "caliper" is used nonrestrictively. Any other appropriate expression may be used to describe the instrument 10, such as medio-lateral digitizer.

In the illustrated embodiment, the legs 12 of FIG. 1 each comprise a translational joint 13 so as to be expandable or contractible along the Y axis. For instance, the translational joints 13 may be any of sliding joint, telescopic joint, prismatic joint, indexing joint, etc. As an alternative, a single one of the legs may have a joint. It is also considered to use rotational joints as an alternative to translational joints 13, with an axis of the rotational joint being normal to a plane of the caliper instrument 10. A locking mechanism is typically provided, to lock the translational joints 13 and, therefore, set the legs 12 in a selected length. The free end of each leg 12 has an abutment end 14, for which any appropriate shape is considered, such as flat contact surfaces, discs, various concavities or convexities, pointy ends, etc., as a function of the type of bone or bodily part the caliper instrument 10 will be contacting. The flat ends 14 of FIG. 1 are well suited to be used with a pelvis, with the ends 14 contacting the anterior superior iliac spines (ASIS) on opposite sides of the pelvis, in pelvic surgery, with the patient in supine decubitus. Alternatively, the caliper instrument 10 could be used for the posterior superior iliac spine as well, among other possibilities.

Still referring to FIG. 1, the legs 12 are interconnected by an elongated body 20 of the caliper instrument 10. The elongated body 20 features a translational joint 21 such that the elongated body 20 is expandable or contractible along the X axis. The translational joint 21 may be any appropriate joint, such as translational joints, telescopic joint, prismatic joints and/or indexing joints. It is also considered to use rotational joints as an alternative to the translational joint 21.

A locking mechanism may be provided, thereby allowing the user to set the length of the elongated body 20. An inertial sensor support or receptacle 23 is defined on the elongated body 20. The inertial sensor support 23 is, for instance, made with a specific geometry in order to precisely and accurately accommodate an inertial sensor unit in a predetermined complementary connection, simplifying an initialization between an inertial sensor unit 26 (FIG. 2) and caliper instrument 10. For instance, the inertial sensor unit has a preset orientation that is aligned with a dimension of the caliper instrument 10. In other words, the mechanical constraints in the attachment of inertial sensor unit in the support 23 are such that the three axes of the inertial sensor unit are aligned with the X, Y and Z axis of the caliper instrument 10. Therefore, the caliper instrument illustrated in FIG. 1 may expand and contract along both the X axis and the Y axis. A light source 24 is also provided on the caliper instrument 10. The light source 24 is of the type producing a planar beam, such that a projection of the planar beam on a surface produced a line. The light source 24 may be on a carriage 25 so as to be displaceable in translation along the elongated body 20. Alternatively, it is considered to configure the carriage 25 to be snap-fitted to the elongated body 20, so as to allow its installation at any position along the elongated body 20.

The inertial sensor unit 26 used with the caliper instrument 10 may have any appropriate type of inertial sensor, to provide 3-axis orientation tracking. For instance, the inertial sensor unit may have sets of accelerometers and/or gyroscopes, etc. The inertial sensor unit may be known as a sourceless sensor unit, as a micro-electro-mechanical sensor unit, etc. As mentioned above, the inertial sensor unit is matingly received in the inertial sensor support 23 in a predetermined complementary connection, such that the initializing of the inertial sensor unit will have the inertial sensor unit specifically oriented relative to the X-Y-Z coordinate system illustrated in FIG. 1 (with the Z axis being the cross-product of the X and Y axes).

The inertial sensor unit 26 uses inertial sensor readings to continually calculate the orientation and velocity of a body without the need for an external reference, i.e., no signal transmission from outside of the sensor assembly is necessary, the inertial sensor unit 26 is self-contained. This process is commonly known as dead-reckoning and forms part of the common general knowledge. An initial orientation and velocity must be provided to the inertial sensor unit 26, i.e., the X-Y-Z coordinate system of FIG. 1, after which the orientation is tracked by integrating the angular rates of gyroscope readings at each time step. With an accurate estimate of the orientation of the inertial sensor unit 26 with respect to the Earth frame of reference, gravitational effects can be removed and inertial forces acting on the accelerometers can be integrated to track changes in velocity and position. Since the inertial sensor unit 26 has no need for an external reference, it may be immune to environmental factors such as magnetic fields and operate under a wide range of conditions.

Figure 2:
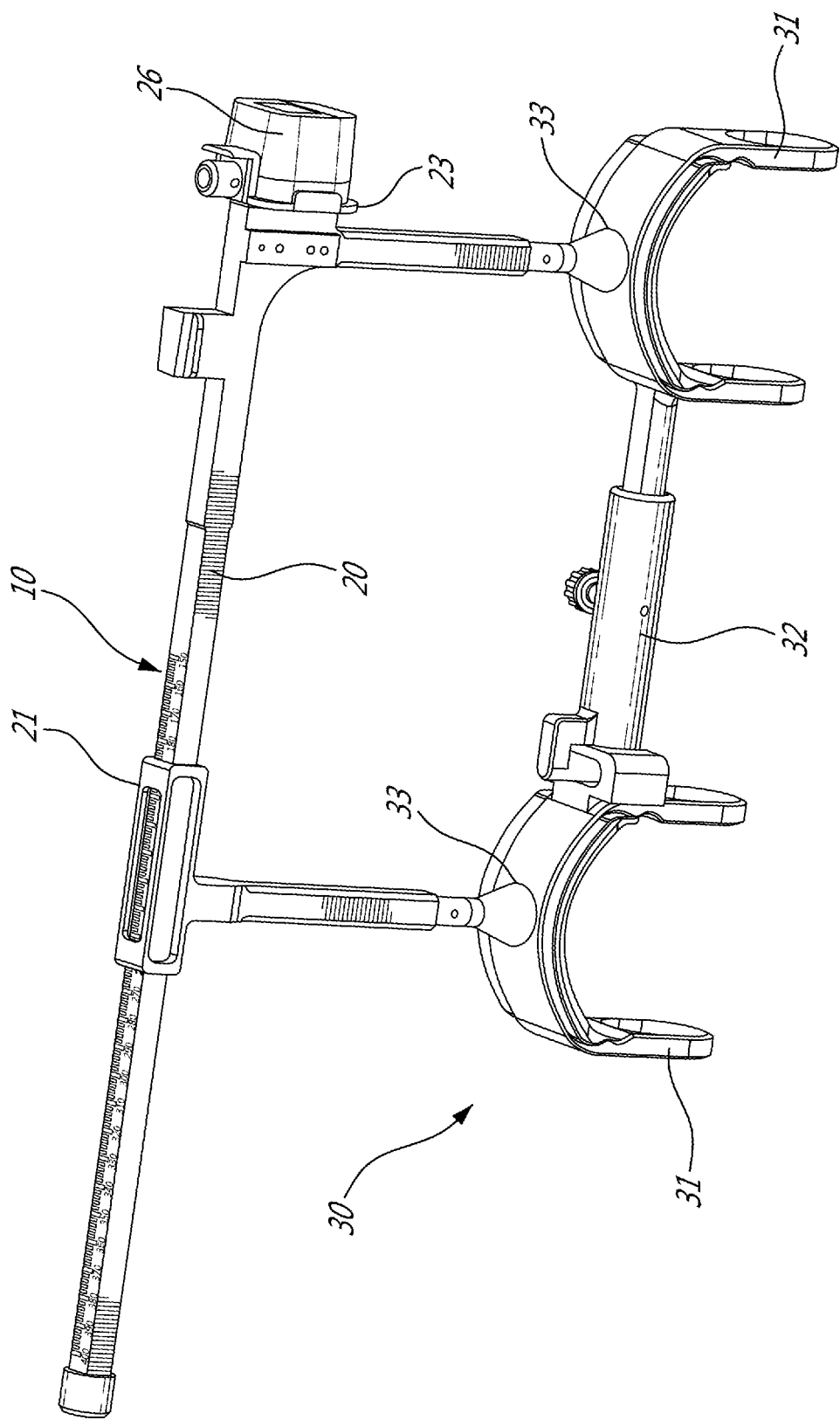
FIG. 2 is a perspective view of the caliper instrument on a mechanical ankle clamp.

Referring to FIG. 2, a mechanical clamp 30 is illustrated. The mechanical clamp 30 has ankle hoops 31 or like ankle attachments or interfaces, separated by a lockable translation joint 32. Hence, a distance between the ankle hoops 31 may be adjusted. The distance between the two ankle hoops 31 can be read from a scale on the joint 32. The ankle hoops 31 are illustrated as being inverted U-shaped structures. According to an embodiment, the hoops 31 each abut against the pair of ankle malleoli, such that the interconnection between the hoop 31 and respective ankle is stable and reproducible. For this purpose, the hoop 31 may have cavities 31A to accommodate the malleoli. Other configurations are considered, including different shapes for the hoops 31, with straps, other joint sets, etc.

The mechanical clamp 30 may have visual indicators 33 to receive therein the ends 14 of the caliper instrument 10 in the manner shown in FIG. 2, to use the scale of the caliper instrument 10, and also ensure precise and reproducible alignment between caliper instrument 10 and mechanical clamp 30, such that the interconnection between the caliper instrument 10 and the mechanical clamp 30 is reproducible from a pre-operative to a post-operative interaction. The visual indicators 33 may identify the center of two malleoli on both ankles, when the mechanical clamp 30 is used. Moreover, the ankle hoops 31 may translate longitudinally with respect to one another (i.e., along the leg), by way of lockable translational joint 34. Other types of joints (i.e., linkages) may also be used to allow relative movement between the ankle hoops 31 and the lockable translation joint 32. For example, the lockable translation joint 32 may have hinges at its ends, by which it would be connected to the ankle hoops 31. Accordingly, the ankle interfaces 31 may remain in a fixed relation with the ankles, while the various joints described herein allow relative movement between the ankles. The visual indicators 33 are positioned such that any relative movement between a pre-operative condition and a post implant rejointing condition can be quantified as described below.

Referring to FIGS. 5, 6, 7 and 8, a mechanical gauge in accordance with the present disclosure is shown at 40, and is another of the instruments that may be used to implement the method of the present disclosure. The mechanical gauge 40 is of the type using a pair of pins 41, though pin holes 42 located at opposed ends of the mechanical gauge 40. A scale 43 is provided on a lockable translational joint 44 of the gauge 40. Accordingly, the mechanical gauge 40 can be used to measure distances. In an embodiment, the mechanical gauge 40 is biased to a zero reading on the scale 43.

Referring to FIGS. 3, 4, 7 and 8, an impactor is shown at 50. The impactor 50 is of the type used in impacting an acetabular cup implant in the acetabulum, for instance as described in in PCT International Publication No. WO 2014/197988, incorporated herein by reference. The impactor 50 may be used as one of the instruments to measure the leg length discrepancy and the offset, for the simple reason that may already be used for the implant procedure. The impactor 50 has the light source 51 allowing its alignment, and an inertial sensor unit 52 similar to the unit 26, containing a gyroscope for dead-reckoning.

Figure 13:
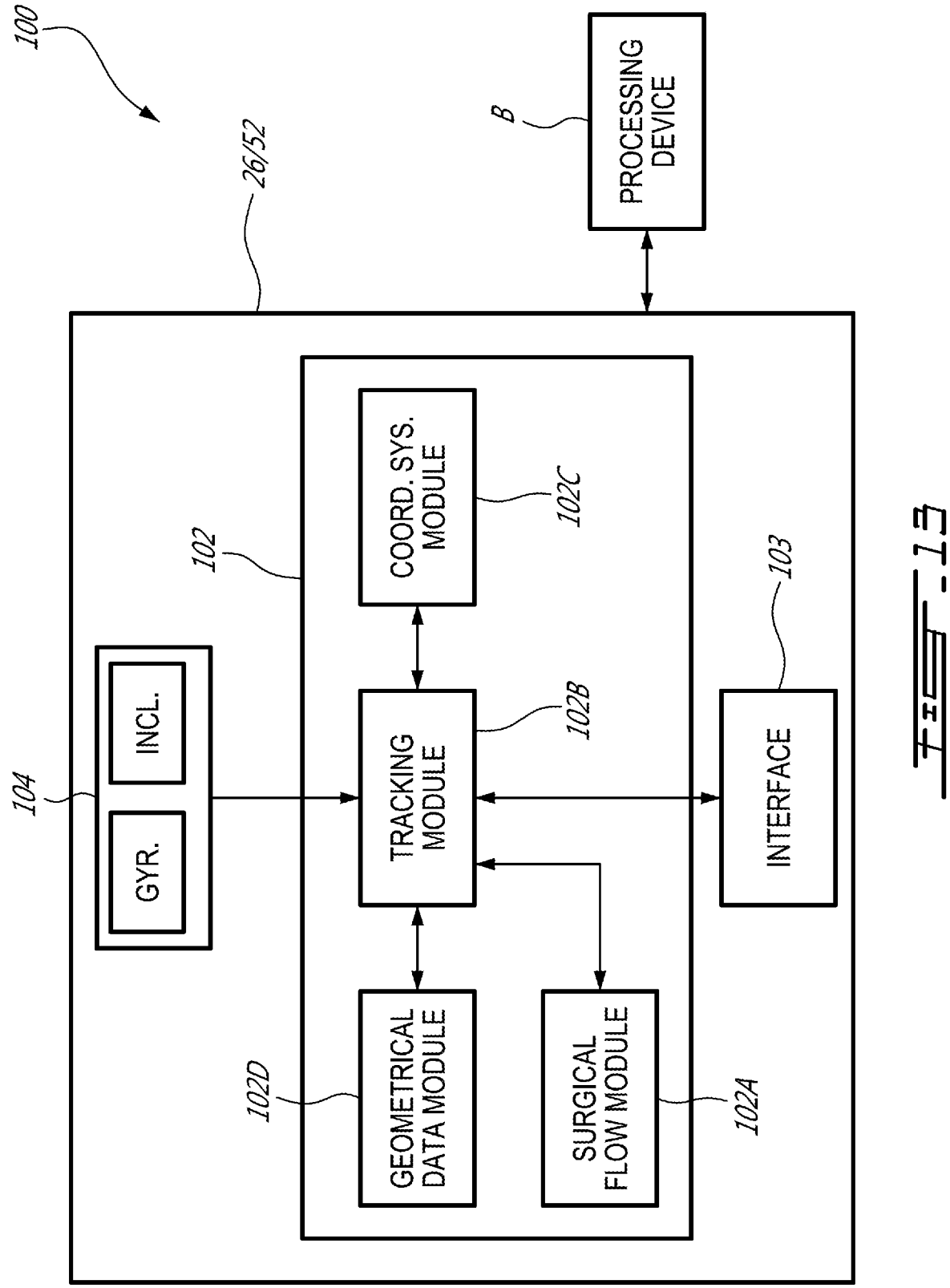
FIG. 13 is a block diagram showing a computer-assisted surgery system operating with instruments to calculate leg length discrepancy and offset, in accordance with the present disclosure.

Referring to FIG. 13, a system for navigating the instruments described above in computer-assisted hip surgery is generally shown at 100, and is of the type used to implement the method detailed below. In an embodiment, the system 100 is used for assisting the user in performing hip surgery, but also has the modules to perform the leg length discrepancy and offset calculations described herein. The system 100 comprises a computer-assisted surgery (CAS) processing unit 102. The CAS processing unit 2 may be integrated into one or more inertial sensor units 26 and 52, also known as pods that are mounted to the various instruments of the system 100, or as a module of a computer or portable device, among other possibilities.

The inertial sensor units 26 and 52 incorporate the processing unit 102 and may thus be equipped with a user interface(s) 103 to provide the navigation data, whether it be in the form of LED displays, screens, numerical displays, etc. Alternatively, the inertial sensor unit 26 and 52 may be connected to a stand-alone processing device B that would include a screen or like monitor, to provide additional display capacity and surface. By way of example, the processing device B is a wireless portable device such as a tablet in a wired or wireless communication with the inertial sensor unit 26/52.

The inertial sensor unit 26/52 may be known as micro-electro-mechanical sensors (MEMS) and may include one or more of inertial sensors, such as accelerometers, gyroscopes, magnetometers, among other possible inertial sensors. The inertial sensors are sourceless sensors automatically providing data influenced by natural phenomena, such as gravity. The inertial sensor unit A also have a body, typically defined by a casing, giving the inertial sensor unit A, by which the inertial sensor unit A may be secured to the instruments.

The processing unit 102 comprises different modules to perform the navigation. A surgical flow module 102A may be used in conjunction with the user interface 103 or a processing device B to guide the operator through the steps leading to the navigation. This may entail providing a step-by-step guidance to the operator, and prompting the operator to perform actions, for instance pressing on a "record" interface that is part of the interface 103 or entering data as measured from the scales of the caliper instrument 10 or mechanical gauge 40, for the system 100 to record instant orientations and position data. While this occurs throughout the surgical procedure, the prompting and interactions between the system 100 and the user will not be described in a remainder of the description, as they will implicitly occur. It is contemplated to have the surgical flow module 102A present in the processing device B, with concurrent action between the inertial sensor unit A and the processing device B to guide the operator during the measuring procedures detailed below, and with a communication with the operator to record the progress of the procedure.

A tracking module 102B may also be part of the processing unit 102. The tracking module 102B receives readings from the inertial sensors 26/52, and converts these readings to useful information, i.e., the navigation data. As described above, the navigation data may be orientation data relating an instrument to the pelvis. The tracking module 102B may perform dead-reckoning to track the inertial sensors 26/52, as described below.

The coordinate system module 102C creates the coordinate system. The coordinate system is the virtual frame by which the orientation of the instruments and tools is related to the orientation of the bone. For example, the coordinate system module 102C sets a pelvic coordinate system from readings of the inertial sensor 26/52 when instruments are in a given orientation relative to the pelvis.

In order to output the record orientations at discrete desired orientations and calculate offset and leg length discrepancy, via the user interface 103 or processing device B, the processing unit 102 may be preprogrammed with geometrical relation data module 102D. The geometrical relation data module 102D is therefore used to record orientations of the various instruments supporting the inertial sensors 26/52, and uses these orientations along with distances to calculate the leg length discrepancy and/or the offset.

The inertial sensor units 26/52 are designed such that they are connected in single possible orientation to the instruments and tools, such that the orientation of the inertial sensor units 26/52 is known relative to the instruments and tools to which it is connected when turned on. By way of the connector 5, the inertial sensor units A may be portable and detachable units, used with one device/instrument, and then transferred to another device/instrument, preserving in the process orientation data of the global coordinate system, using dead-reckoning.

The geometrical relation data module 102D is programmed for specific use with the devices and instruments described herein. Accordingly, when an inertial sensor unit is mounted to one of the devices and instruments, the relation between the device/instrument and a coordinate system of the inertial sensor unit is known (in contrast to a global coordinate system) by the geometrical relation data module 102D. For example, the relation may be between an axis or a 3D coordinate system of the device/instrument and the coordinate system of the inertial sensor unit A.

The navigation of instruments is intended to mean tracking at least some of the degrees of freedom of orientation in real-time or quasi-real time, such that the operator is provided with navigation data calculated by computer assistance. The inertial sensors A used in the following method may be interrelated in the global coordinate system (hereinafter, coordinate system), provided appropriate steps are taken to record or calibrate the orientation of the inertial sensors A in the coordinate system. The coordinate system serves as a reference to quantify the relative orientation of the different items of the surgery, i.e., the instruments and devices relative to the pelvis.

The present application contemplates different techniques to provide the leg length and offset measurements. In general, the techniques each comprise two procedures, i.e., leg positioning, and taking the leg length and/or offset measurements. The following paragraphs set out different techniques to measure leg length discrepancy and offset, between a pre-operative condition, and a post-operative condition, using some of the instruments described above. For clarity, the expression post-operative is used herein as representative of a part of the procedure after positioning of the implant on the bone, when the leg can be rejointed, i.e. post-implant rejointing. However, post-operative includes intra-operative, in that the measurements may be taken before the end of the procedure, to allow corrective measures to be taken, for example. Hence, throughout the text, the use of the expression "post-operative" includes intra-operative interventions. The techniques that do not use the mechanical gauge 40 are non-invasive, in that they may be used over the skin, or in that they do not require patient tissue alterations other than the ones required for surgery.

Procedure of Leg Positioning

The purpose of this procedure is to position or reposition the leg along the longitudinal axis of the patient (a.k.a., cranial-caudal axis), in a reproducible manner. If the leg is laid flat on the table, this leg positioning may enable alignment of the leg with the frontal plate of the patient. In order to measure offset and leg length discrepancy precisely and accurately, the leg positioning must be replicated between measurements. The impact on the measurements of the leg length discrepancy introduced by misalignment of the leg is minimized by the use of this procedure. The procedure is performed as follows:

1. The patient is placed in supine decubitus.
2. Referring to FIG. 1, the caliper instrument 10 is placed on two pelvic landmarks, after being telescopically arranged to have a suitable length. For example, the caliper instrument 10 is placed on the two anterior-superior iliac spines, in the manner shown in FIG. 1. An assumption is made that the caliper instrument 10 is aligned with the medio-lateral axis of the patient. A light beam is shone from the light source 24 that is attached to the caliper instrument 10. The light source 24 is connected to the frame of the caliper instrument 10 such that the light beam is projected distally and perpendicular to the frame of the caliper instrument 10, and therefore parallel to the longitudinal axis of the patient, a.k.a., the cranial-caudal axis, in direction Z of FIG. 1. The user is required to align the first leg with the projected light beam, by manually displacing it.
3. Different approaches are considered for the alignment. For instance, as the light beam produces a line, the user may align the light beam line with leg landmarks. For example, a center of the knee cap and a center of the ankle to be shone by the light beam line. Temporary pen or ink markings may be made on the knee and/or ankle to indicate the landmarks used for alignment.
4. The light source 24 is then slid along the caliper instrument 10, using carriage 25. The light beam is therefore translated laterally. As a result, the second leg can be aligned in the same way, by manually displacing it, as guided by the selected landmarks. Since the light beam is perpendicular to the caliper instrument 10—and hence also perpendicular to the medio-lateral axis of the patient—, the light beam indicates the projection of the sagittal plane on the patient. As an alternative to assuming this, the table plane can be assessed by a pod to determine if the table plane is leveled. Once aligned using the light source 24 in the manner described above, the assumption is made that the legs are physically aligned with respect to the longitudinal axis. Moreover, as the patient is in supine decubitus, it can be assumed that the legs are within the frontal plane. As a result, the leg is along the longitudinal axis (i.e. the intersection of both sagittal and frontal planes). Based on these assumptions, the leg length discrepancy can be measured along the longitudinal axis. The offset can be measured along the medio-lateral axis. This is achieved by comparing data obtained from the instruments described above, between pre-operative measurements, and intra-operatively and/or post-operative measurements.

Procedure: leg length discrepancy and/or offset measurements

Numerous techniques are possible for this procedure, as described below with reference to the figures.

Technique 1: the instruments required are the caliper instrument 10, or alternatively the impactor 50, with light source 24 and dead-reckoning of the inertial sensor unit 26 or 52, to measure leg length discrepancy.

Figure 3:
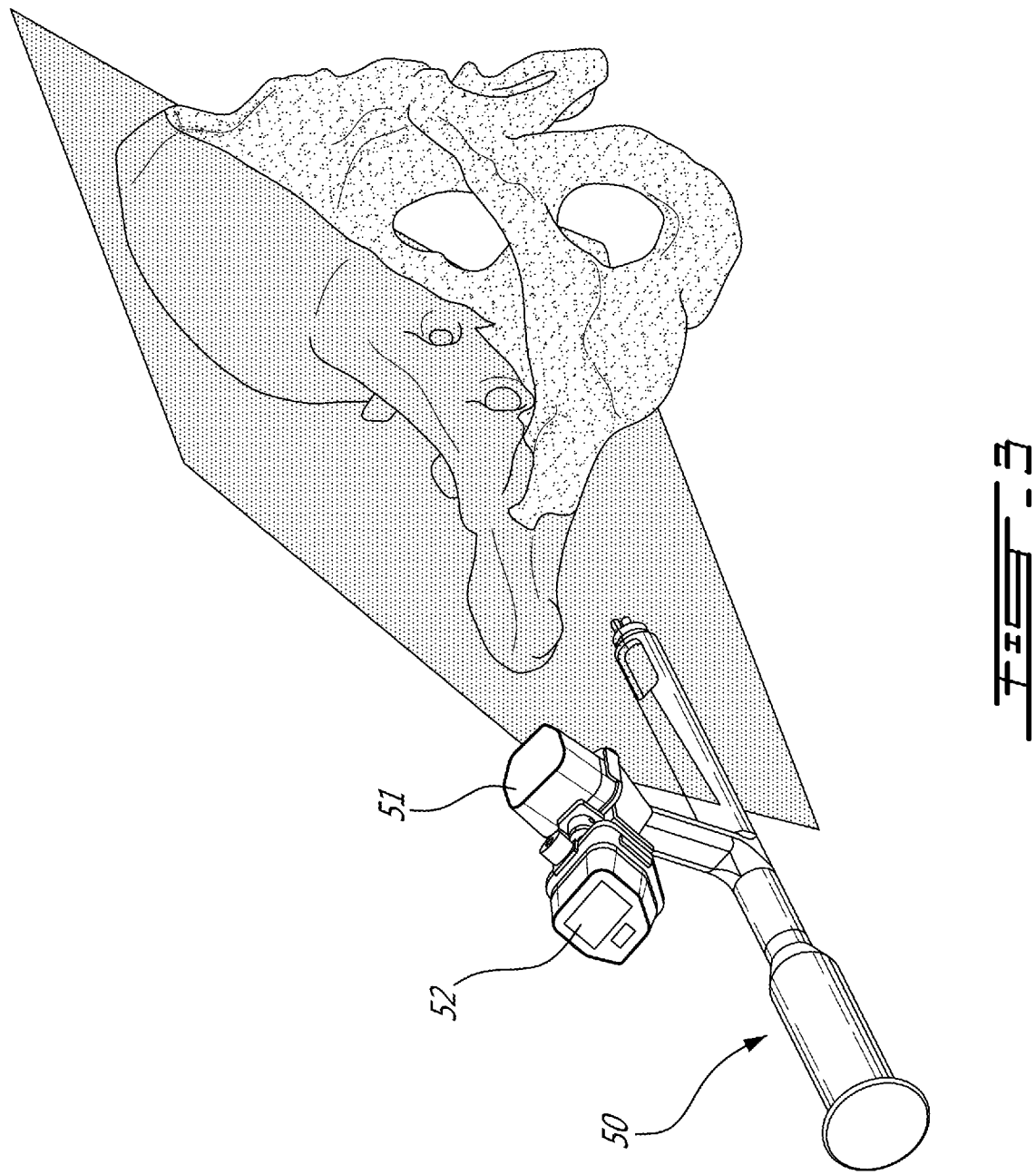
FIG. 3 is a perspective view of an impactor using in leg length and offset measurement relative to a pelvis.
Figure 4:
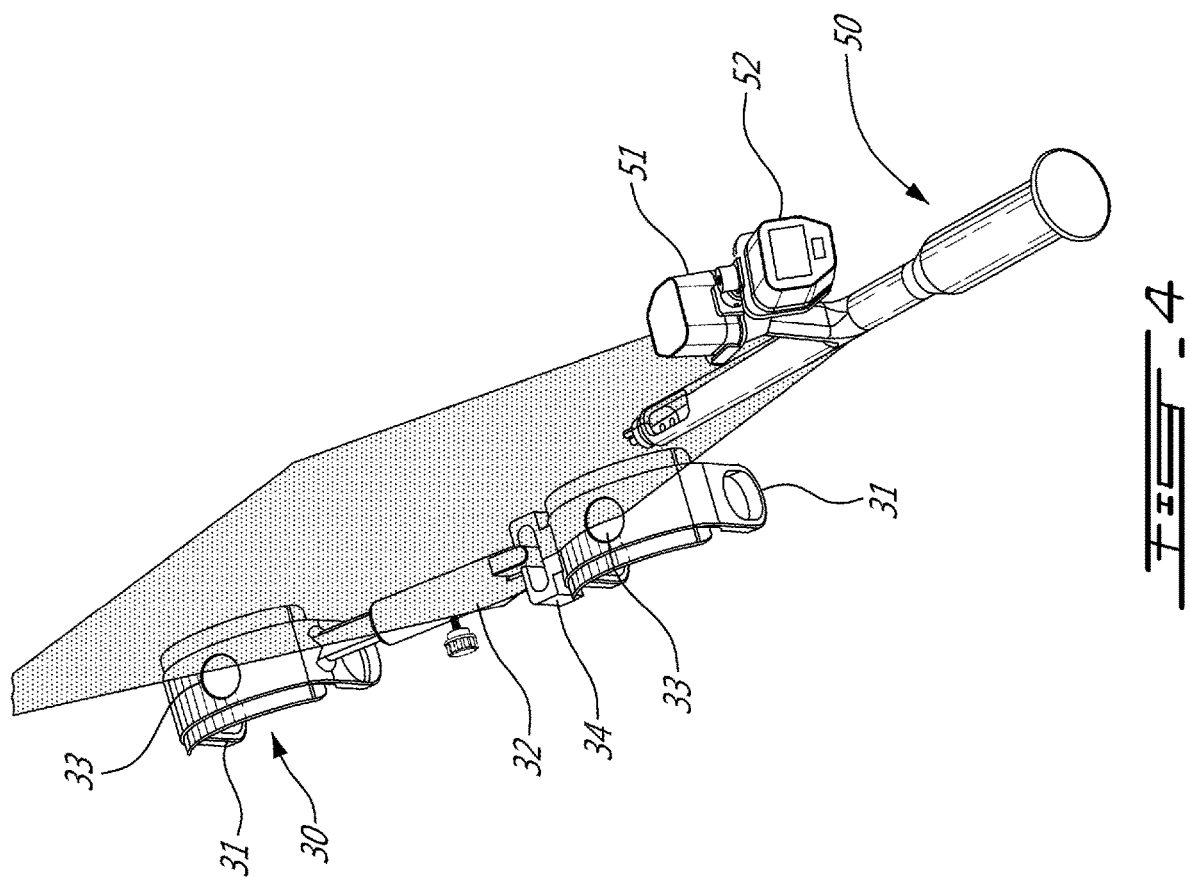
FIG. 4 is a perspective view of an impactor using in leg length and offset measurement relative to the mechanical ankle clamp.

1. Referring to FIG. 2, with the patient's legs positioned using the leg positioning procedure mentioned above, the mechanical clamp 30 is rigidly attached to the ankles of the patient;
2. The first medio-lateral axis, i.e., that of the pelvis, is acquired by using the caliper instrument 10 in the manner described above, or the impactor 50. The impactor 50 may be navigated to determine the medio-lateral axis, for instance as described in PCT International Publication No. WO 2014/197988, incorporated herein by reference. For example, the light beam of the light source is in a known relation relative to a shaft of the impactor 50;
3. After acquiring the pelvic medio-lateral axis, the caliper instrument 10 is moved to the ankles to acquire a second medio-lateral axis, near the feet. For example, the second medio-lateral axis, i.e., the leg medio-lateral axis, may be defined by the line connecting the two centers of both ankles (as in FIG. 2), thus making use of the visual indicators of the mechanical clamp 30 to physically provide these landmarks. In the arrangement of FIG. 2, the caliper instrument 10 is in a position to record the medio-lateral axis at the ankle;
4. In the acquisition of the medio-lateral axes, the inertial sensor unit 26 attached to the caliper instrument 10 (or impactor in alternative embodiment) contains a gyroscope. The gyroscope will provide data that is then used by a CAS processing unit to perform dead-reckoning and hence acquire the relative orientation between the two medio-lateral axes, $\alpha_{preop}$, i.e., at the hip (FIG. 1) and at the ankles (FIG. 2);
5. During or upon finishing the hip surgery, with the operated leg rejointed, the angle $\alpha_{postop}$ between two medio-lateral axes is obtained by repeating steps 1-4. The same leg positioning technique is used prior to taking the measurements to ensure the legs are positioned in the same way as preoperatively, i.e., parallel to the sagittal plane;
6. Based on the known distance between the two ankles (D) as obtained from the scale on the joint 32 (e.g., scale 21) and the angular difference in a, the leg length discrepancy can be resolved as: $D \cdot \tan(\alpha_{postop}) - D \cdot \tan(\alpha_{preop})$. A positive value would mean a longer leg post-operatively, whereas a negative value would mean a shorter leg post-operatively. FIGS. 3 and 4 illustrate technique 1 using the impactor alternative. It should be noted that D may vary between a pre-operative measurement and a post-operative measurement, whereby the first D in the solution is D measured post-operatively and the second D in the solution is D measured pre-operatively. It is also contemplated to fix the D, whereby step 5 would not require repositioning the leg as in step 1.

Technique 2: caliper instrument 10 is used for this technique, to measure the offset.

1. The patient's legs are positioned using the leg positioning technique described above, sliding the light source 24 on the caliper instrument 10 to align the projected light beam on both legs, as in FIG. 1;
2. The readings from the inertial sensor unit 26 on the caliper instrument 10 are recorded ($O_{preop}$);
3. Upon finishing the hip surgery, steps 1-2 are repeated to acquire the readings ($O_{postop}$) from the inertial sensor unit on the caliper instrument 10;
4. The offset can be resolved as: $O_{postop} - O_{preop}$, positive value indicates an increase in the offset and negative value indicates a decrease in the offset.

Figure 5:
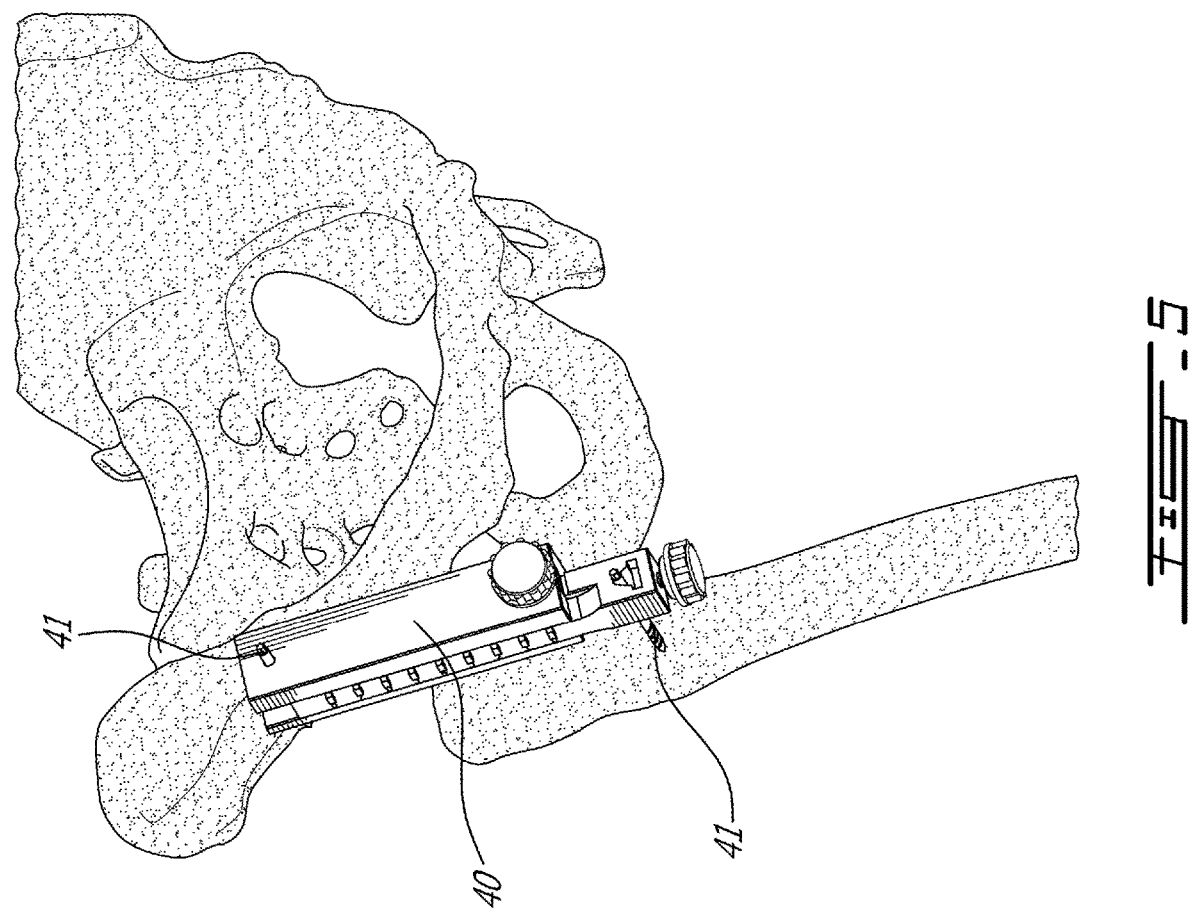
FIG. 5 is a perspective view of a pinned mechanical gauge.
Figure 6:
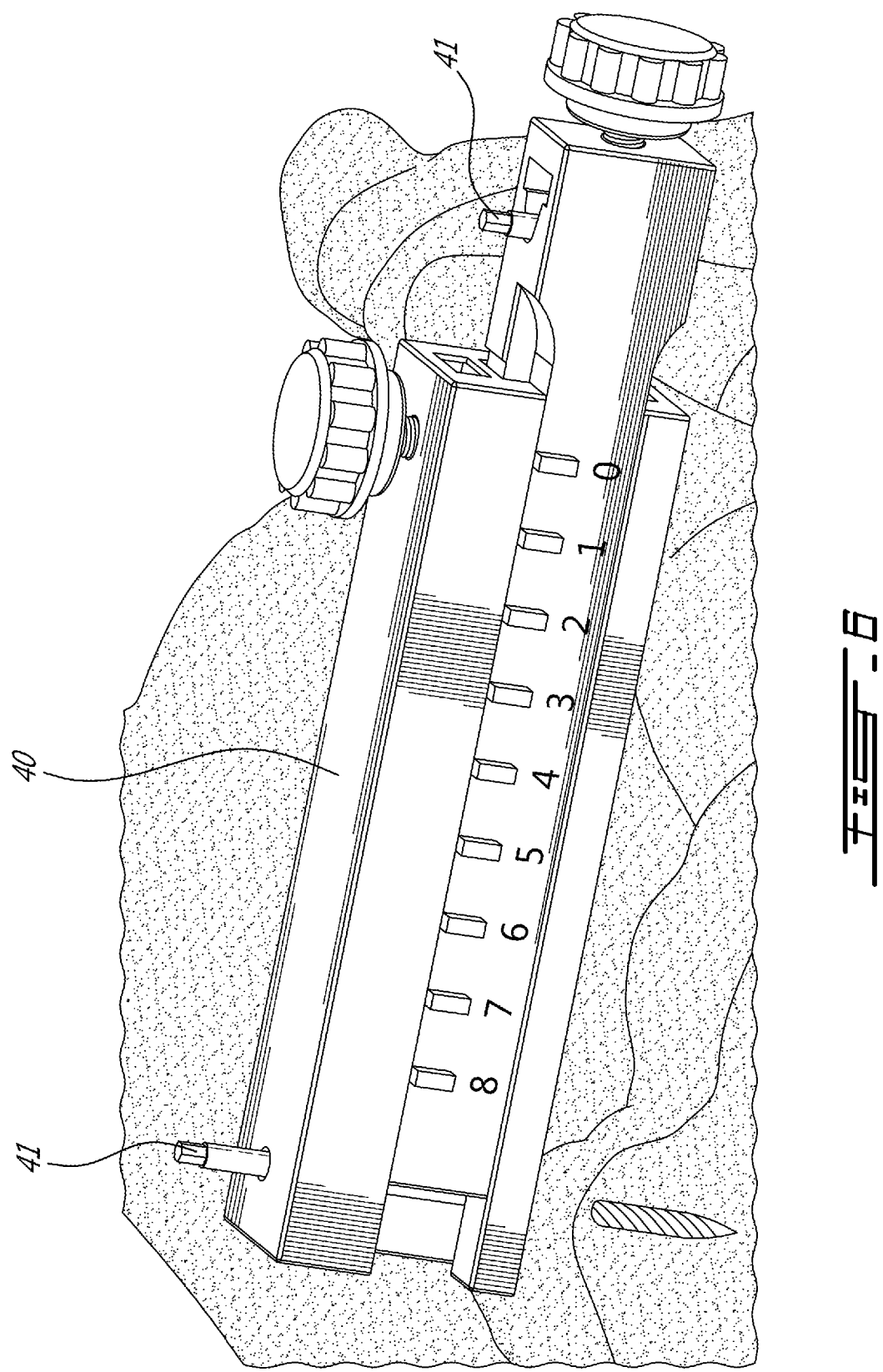
FIG. 6 is an enlarged perspective view of the pinned mechanical gauge.
Figure 7:
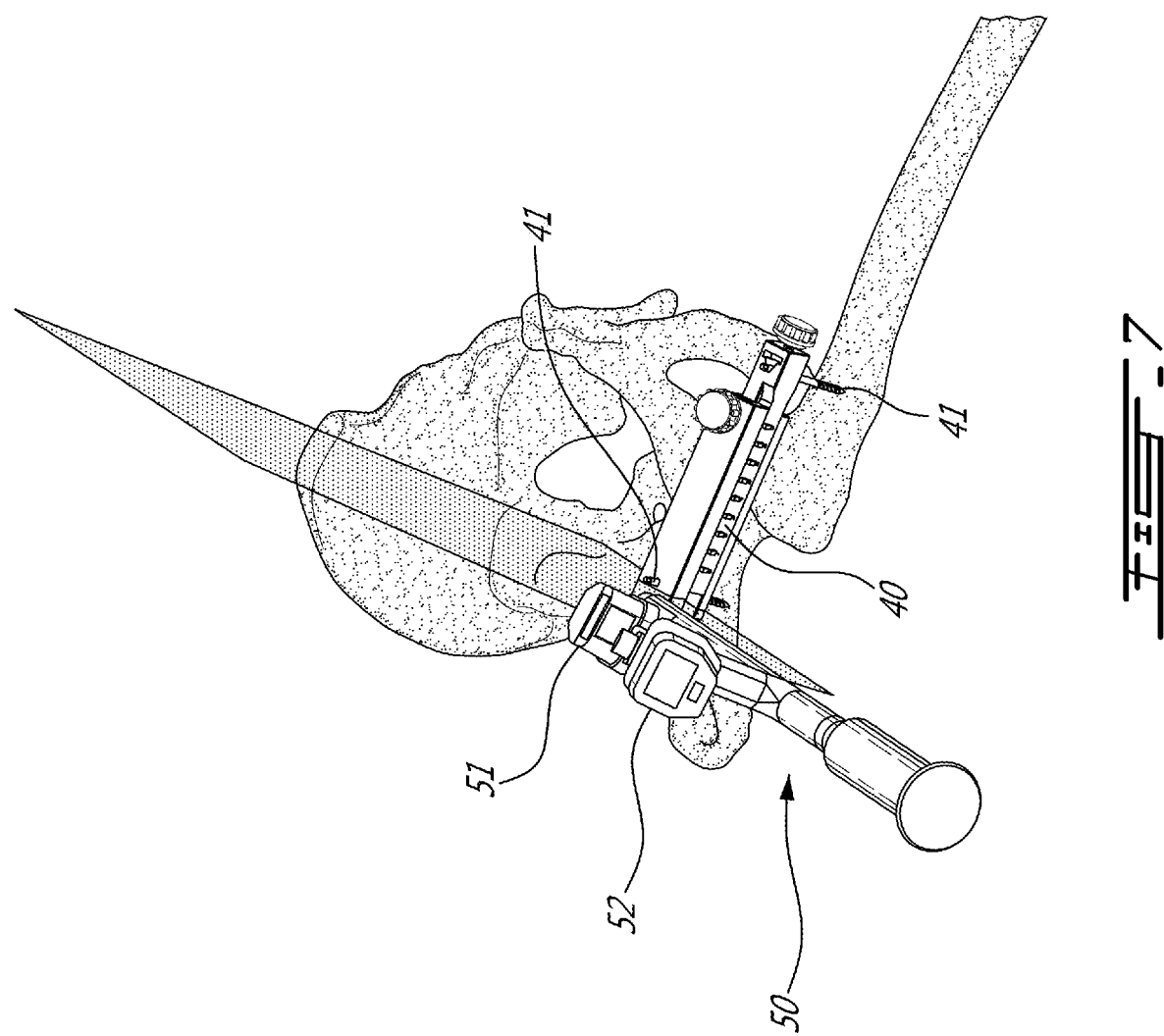
FIG. 7 is a perspective view of a pinned mechanical gauge and impactor.
Figure 8:
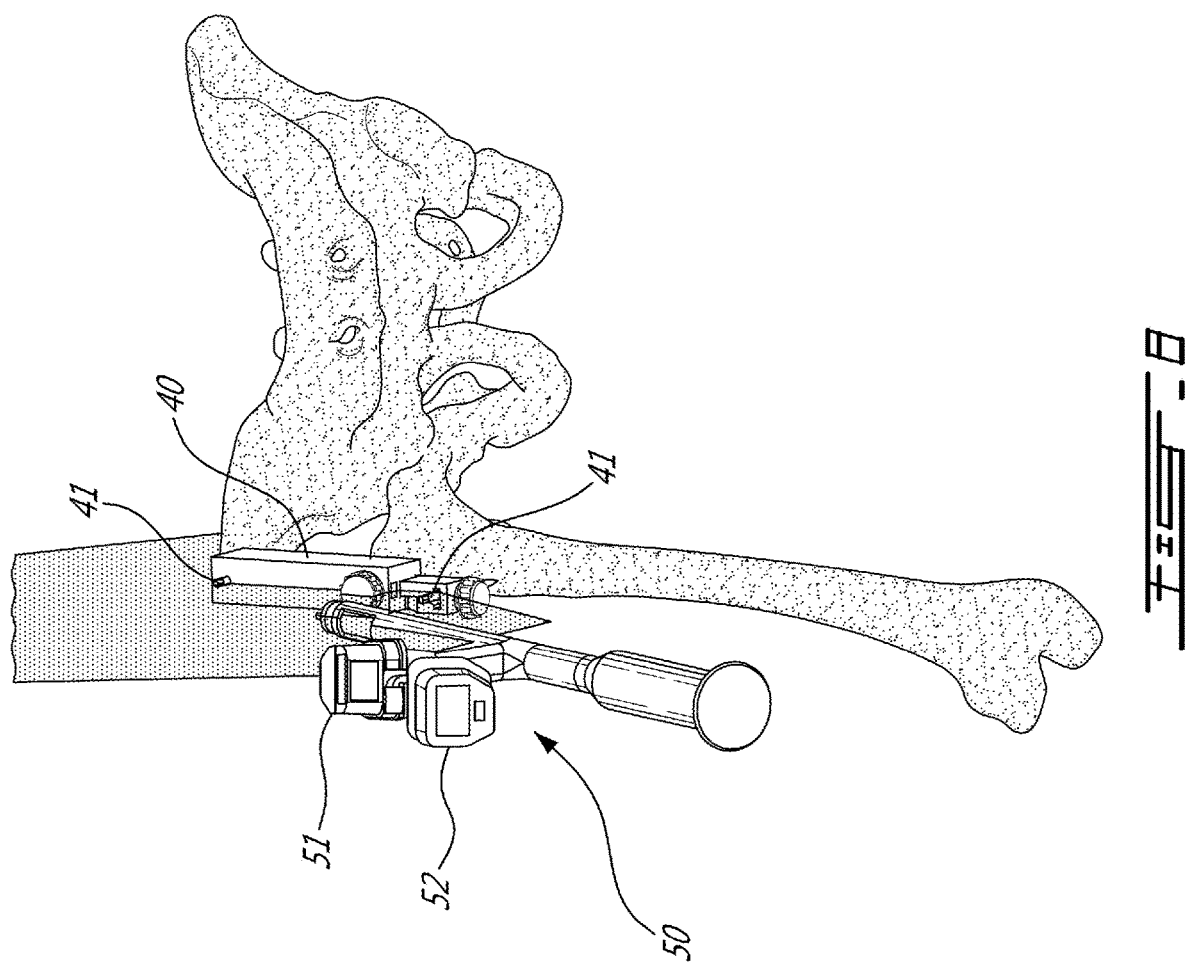
FIG. 8 is a perspective view of the pinned mechanical gauge and impactor.

Technique 3: this technique uses the mechanical measuring gauge 40 and dead-reckoning.
1. The patient's legs are positioned using the leg positioning technique.
2. Prior to cutting the femoral neck and preparation of the acetabulum, as shown in FIGS. 5 and 6, a first pin 41 is fixed on the ASIS and another pin 41 is fixed on the greater trochanter area; both pins 41 are on the operated side. The pins 41 respectively constitute a pelvis landmark and a leg landmark;
3. The mechanical gauge 40 is fixed to the two pins 41, and the distance M between the two pins 41 is known from the scale 42 of the gauge 40;
4. The impactor 50 as shown in FIG. 7 is used and firstly aligned with the medio-lateral axis (using the light source 51 thereof to project a light beam on the two ASIS); then, the impactor 50 is aligned using the light source 51 with the long axis of the mechanical gauge 40, as in FIG. 8, showing a landmark orientation. The inertial sensor unit 52 containing a gyroscope to perform dead-reckoning to acquire the angle ($\beta_{preop}$, note $\beta_{preop} < \pi/2$) between the medio-lateral axis and the long axis of the mechanical gauge 40;
5. The gauge 40 is removed, while the pins 41 are kept on the femur and pelvis, at which point the user may proceed with the femoral procedure;
6. Upon finishing placing the femoral implant and/or the acetabular component and rejointing the leg (intra operatively or post operatively), the distance of the gauge 40 is adjusted, and the gauge 40 is reattached to the two pins 41. The angle ($\beta_{postop}$, note $\beta_{postop} < \pi/2$) are acquired between the medio-lateral axis and the long axis of the gauge 40 by repeating step 4-5; The same leg positioning procedure is used beforehand to make sure the legs are positioned in the same way as pre-operatively;
7. The leg length discrepancy can be resolved as: $M \cdot \sin(\beta_{postop}) - M \cdot \sin(\beta_{preop})$; The offset can be resolved as: $M \cdot \cos(\beta_{postop}) - M \cdot \cos(\beta_{preop})$. It should be noted that M may vary between a pre-operative measurement and a post-operative measurement, whereby the first M in the solution is M measured post-operatively and the second M in the solution is M measured pre-operatively.

Figure 9:
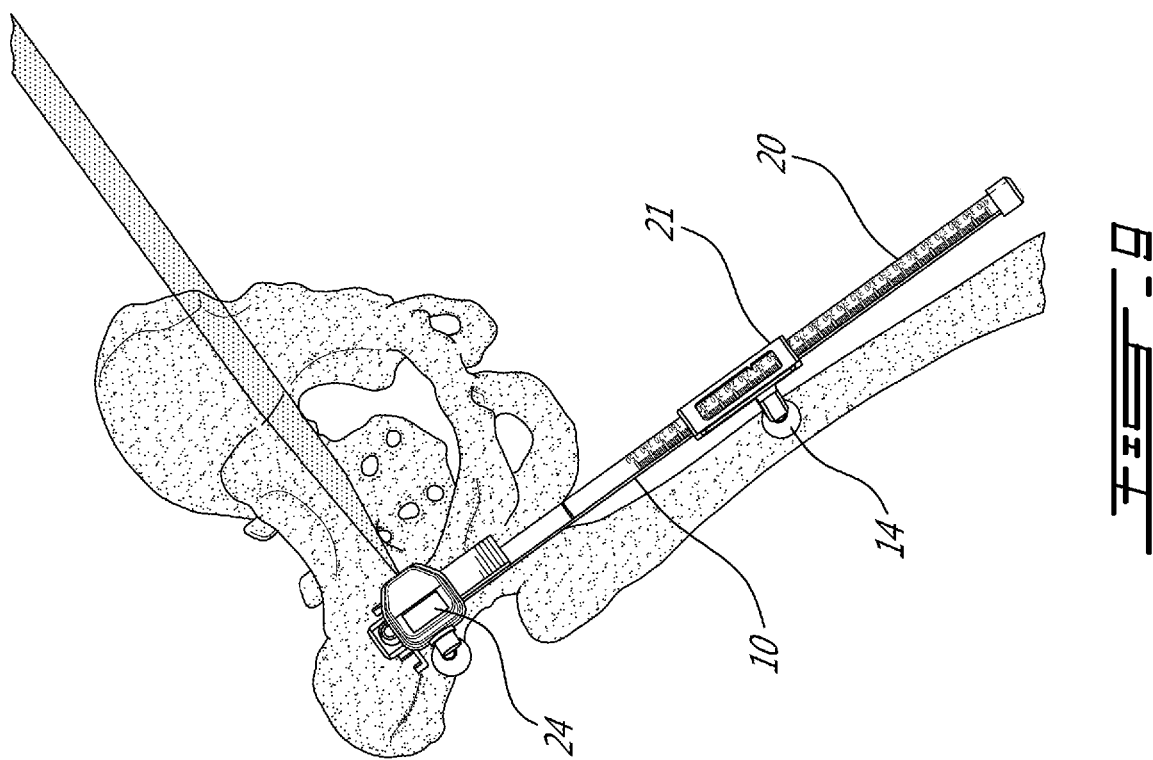
FIG. 9 is a perspective view of the pinned mechanical gauge and caliper instrument.
Figure 10:
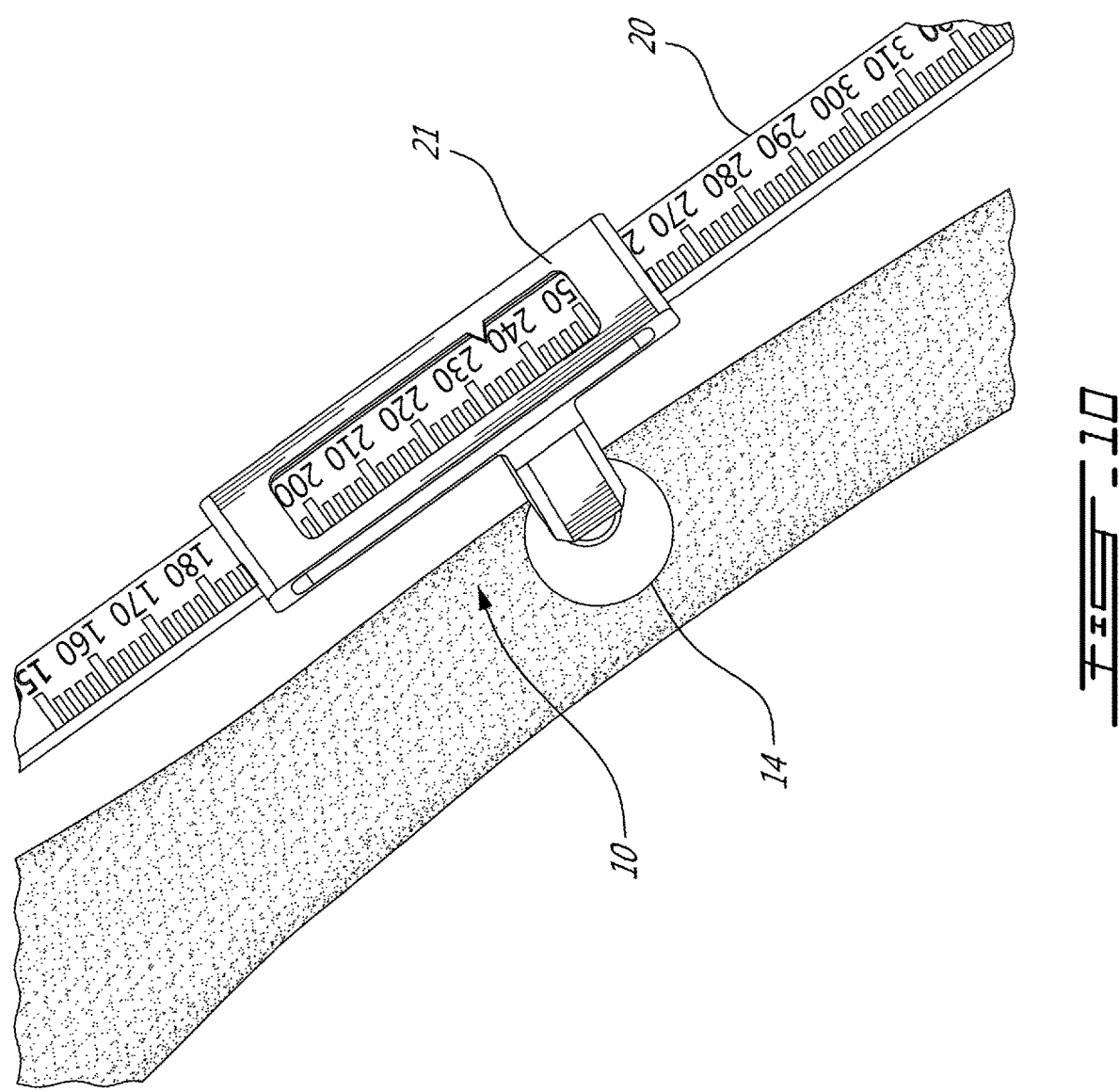
FIG. 10 is an enlarged view of the scale on the caliper instrument.

Technique 4: this technique involves the caliper instrument 10 for a direct measurement of leg length discrepancy (proximal)
1. The patient's legs are positioned using the leg positioning procedure described above;
2. The ends 14 of the caliper instrument 10 are placed on the ASIS of the operated side and on a marked reference on the skin on the femur (e.g., a landmark on the skin), as shown in FIGS. 9 and 10, respectively the pelvic landmark and the leg landmark. The light source 24 is displaced to project its beam on the opposite ASIS, when selecting the marked reference;
3. The initial distance measurement is recorded on the caliper instrument 10 ($N_{preop}$);
4. Upon finishing the surgery, the distance measurement is obtained using the caliper instrument 10 ($N_{postop}$), after repeating the leg positioning procedure, and by repeating steps 2 and 3;
5. The leg length discrepancy can be resolved as: $N_{postop} - N_{preop}$.

Figure 11:
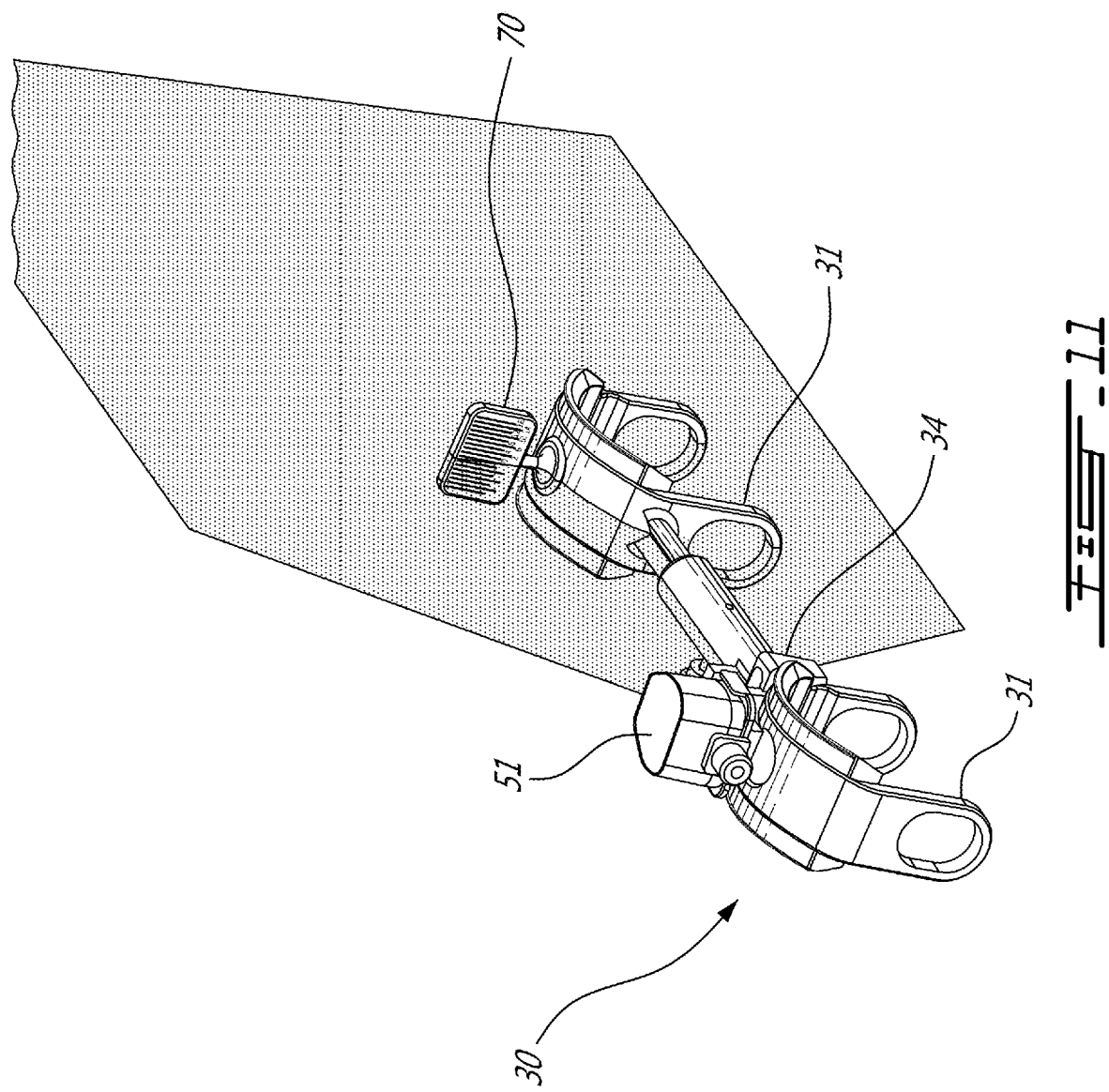
FIG. 11 is a perspective view of the mechanical ankle clamp with light source.
Figure 12:
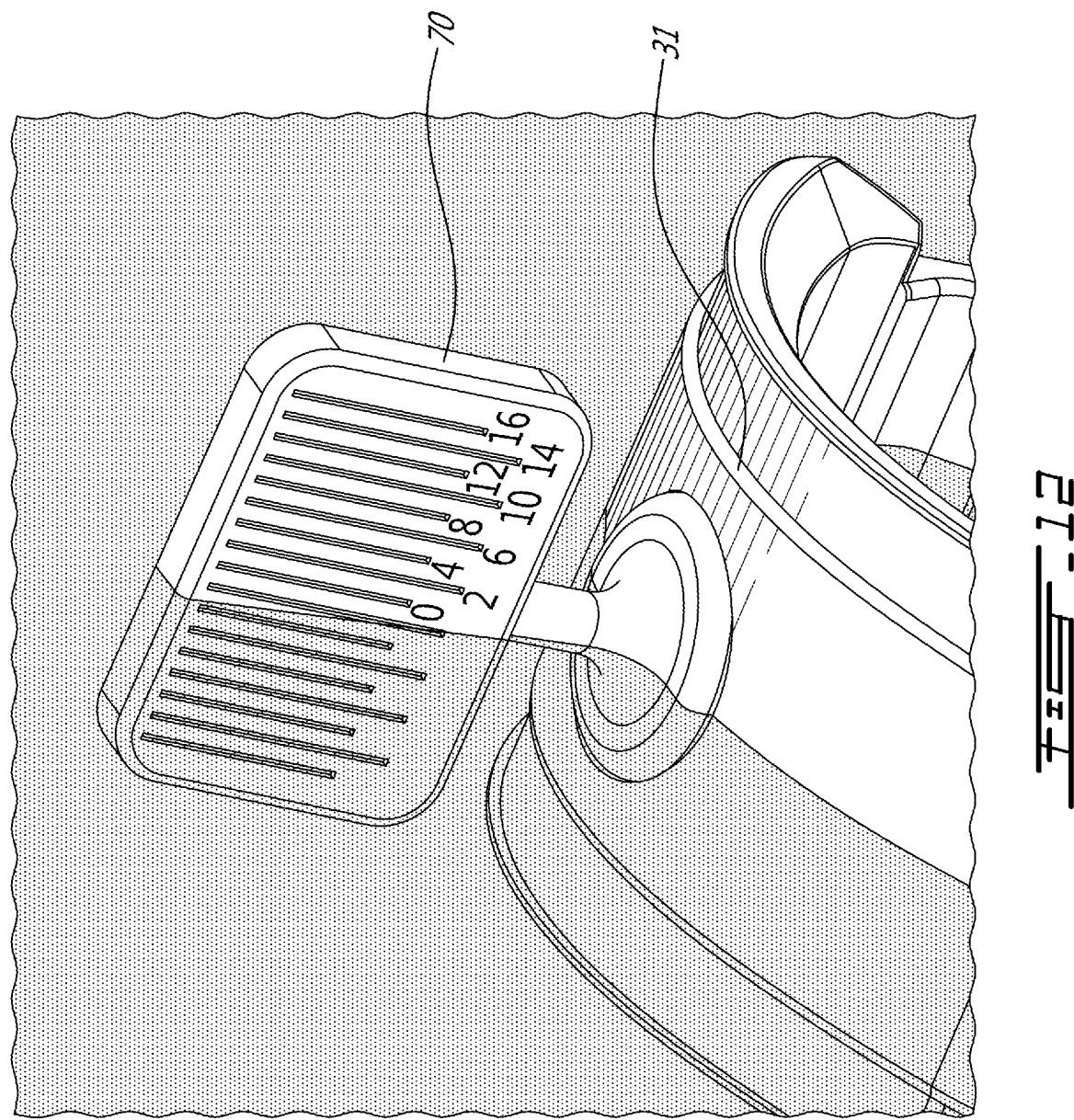
FIG. 12 is an enlarged view of a scale on the mechanical ankle clamp.

Technique 5: Direct measurement of leg length discrepancy (distal), using the caliper instrument 10, the mechanical clamp 30 and using one of the light sources 24 or 51.
1. The patient's legs are positioned using the leg positioning procedure described above;
2. The mechanical clamp 30 is placed on both ankles, in the manner shown in FIG. 2;
3. The light source 51 is connected to the mechanical clamp 30, and is projected on a scale 70 on the operated leg to record the initial leg length ($X_{preop}$), as shown in FIG. 11. Surgery may be initiated, however, the translational joint 34 is unlocked to allow the translation of the ankle hoops 31 relative to one another;
4. Upon finishing the surgery, the distance measurement is obtained using the mechanical clamp 30 ($X_{postop}$) by repeating the steps 1-3; and
5. The leg length discrepancy is resolved as: $X_{postop} - X_{preop}$.

The invention claimed is:

1. A computer-assisted surgery system for outputting at least one of a leg length discrepancy and an offset between a preoperative leg condition and a post-implant rejointing leg condition comprising:
   at least one instrument;
   at least one inertial sensor unit connected to the at least one instrument, the inertial sensor unit producing readings representative of its orientation;
   a computer-assisted surgery processor unit operating a surgical assistance procedure and comprising
      a coordinate system module for setting a pelvic coordinate system from readings of the at least one inertial sensor unit when the at least one instrument is in a given orientation relative to the pelvis,
      a tracking module for tracking an orientation of the at least one instrument relative to the pelvic coordinate system during movements thereof using the readings from the inertial sensor unit on the instrument, and
      a geometrical relation data module for recording pre-operatively a landmark orientation relative to the pelvic coordinate system and a distance when the at least one instrument has a first end abutted to a pelvic landmark and a second end abutted to a leg landmark, for recording after implant rejointing the landmark orientation and said distance, and for calculating at least one of a leg length discrepancy and an offset, based on said distances and said landmark orientations; and
   an interface for outputting at least the leg length discrepancy or the offset between the preoperative leg condition and the post-implant rejointing leg condition.

2. The computer-assisted surgery system according to claim 1, wherein the at least one instrument is a caliper having a body with a translational joint for expanding/contracting, and legs configured for contacting the pelvic landmark and the leg landmark.

3. The computer-assisted surgery system according to claim 2, wherein the caliper supports a light source emitting a light beam that is perpendicular relative to a direction of the translational joint.

4. The computer-assisted surgery system according to claim 3, wherein the given orientation has the light beam illuminating the medio-lateral axis of the pelvis.

5. The computer-assisted surgery system according to claim 2, further comprising a scale on the translational joint to obtain said distances.

6. The computer-assisted surgery system according to claim 2, wherein the caliper supports a light source emitting a light beam that is parallel relative to a direction of the translational joint.

7. The computer-assisted surgery system according to claim 1, wherein the at least one instrument includes a mechanical gauge having a body with a translational joint for expanding/contracting, and bores configured for being connected to pins constituting the pelvic landmark and the leg landmark.

8. The computer-assisted surgery system according to claim 7, further comprising a scale on the translational joint to obtain said distances.

* * * * *